United States Patent [19]

Urano et al.

[11] Patent Number: 4,666,993

[45] Date of Patent: May 19, 1987

[54] FUNCTIONAL POLYMERS AND THEIR PRODUCTION

[75] Inventors: Satoshi Urano, Yawata; Kei Aoki, Ikoma; Takeyasu Ito, Joyo; Yuji Suzuki, Suita; Ryuzo Mizuguchi, Yawata, all of Japan

[73] Assignee: Nippon Paint Co., Ltd., Osaka, Japan

[21] Appl. No.: 867,021

[22] Filed: May 27, 1986

[30] Foreign Application Priority Data

May 27, 1985 [JP] Japan .................................. 60-114481
May 28, 1985 [JP] Japan .................................. 60-117307
May 28, 1985 [JP] Japan .................................. 60-117308
Apr. 22, 1986 [JP] Japan .................................. 61-094297

[51] Int. Cl.$^4$ ............................................ C08G 18/00
[52] U.S. Cl. ............................... 525/328.2; 525/452; 526/248; 526/258; 526/263; 526/266; 526/268; 526/288; 526/303.1; 526/312

[58] Field of Search ................ 525/328.2, 452; 526/248, 258, 263, 266, 268, 288, 303.1, 312

[56] References Cited

U.S. PATENT DOCUMENTS 4,401,794  8/1983  Oriel et al. ..................... 525/328.2

Primary Examiner—Maurice J. Welsh
Attorney, Agent, or Firm—Wegner & Bretschneider

[57] ABSTRACT

A functional polymer having a main chain of carbon-carbon bonds and at least one functional group appended to the main chain with intervention of a carbonyliminocarbonyl linkage, the functional group being any one chosen from the group consisting of a fluorinated group, an aminotriazine group, a photosensitive group and a bicyclo or spiro structure group and the content of the functional groups including the carbonyliminocarbonyl linkage in the molecule of the functional polymer being from 0.1 to 99.9% by weight.

8 Claims, No Drawings

FUNCTIONAL POLYMERS AND THEIR PRODUCTION

The present invention relates to functional polymers and their production. More particularly, it relates to polymers comprising a main chain of carbon-carbon bonds and a functional group as a pendant to the main chain, said functional group being characteristic in connecting to the main chain with intervention of a carbonyliminocarbonyl linkage (—CONHCO—).

In recent years, a great number of polymers are artificially produced and used in various fields, and there are always demands to new polymers having better, enhanced or improved physical properties.

As a result of the extensive study seeking new polymers having excellent physical properties such as high elasticity, good adhesion and favorable dispersibility, it has now been found that polymers having a main chain of carbon-carbon bonds and a functional group appending thereto through a carbonyliminocarbonyl linkage show excellent physical properties attributed to the functional group and the carbonyliminocarbonyl linkage.

Accordingly, a basic object of the present invention is to provide a polymer having a main chain of carbon-carbon bonds and a functional group appending thereto through a carbonyliminocarbonyl linkage. Another object of the invention is to provide an intermediate monomer usable for production of said polymer. A further object of the invention is to provide a process for production of said polymer. These and other objects will be apparent to those skilled in the art from the foregoing and subsequent descriptions.

The functional polymer of the invention is a polymer which comprises a main chain comprising carbon-carbon bonds and at least one functional group appended to the main chain through a carbonyliminocarbonyl linkage, the content of the functional groups (including the carbonyliminocarbonyl linkage) in the polymer being from 0.1 to 99.9% by weight and the molecular weight of the polymer being from 1,000 to 100,000.

Said functional polymer can be produced by two processes, of which one comprises polymerization of an alkenyl isocyanate of the formula:

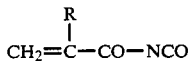

(I)

wherein is a hydrogen atom or a lower alkyl group (e.g. methyl, ethyl, propyl) optionally with one or more polymerizable monomers and addition of a functional group-containing compound having an active hydrogen atom of the formula:

R'—H     (II)

wherein R' is the residue of a functional group-containing compound excluding the active hydrogen atom therefrom to the isocyanatocarbonyl group in the resultant isocyanatocarbonyl group-containing polymer, and the other comprises addition of the functional group-containing compound (II) to the alkenyl isocyanate (I) and polymerization of the resulting functional group-introduced isocyanatocarbonyl group-containing compound optionally with one or more polymerizable monomers.

According to the first process, the functional polymer of the invention can be produced by (1-a) polymerization of the alkenoyl isocyanate (I) optionally with one or more polymerizable monomers to give an isocyanatocarbonyl group-containing polymer and (1-b) addition of the functional group-containing compound (II) to the isocyanatocarbonyl group in the isocyanatocarbonyl group-containing polymer.

In the step (1-a), the polymerization may be carried out by a per se conventional procedure, particularly by solution polymerization. For instance, a monomeric mixture comprising the alkenoyl isocyanate (I) and optionally one or more polymerizable monomers in an inert solvent, preferably comprising a polymerization initiator is maintained at a temperature of 20° to 200° C., favorably of 60° to 150° C., more favorably of 80° to 120° C. for about 0.5 to 5 hours. The content of the alkenoyl isocyanate-(I) in the total weight of the monomers is to be not less than 0.1% by weight. The amount of the polymerization initiator may be, when used, from 0.1 to 10% by weight, preferably from 0.5 to 5% by weight, based on the total weight of the monomers. When desired, a chain transfer agent may be also present in the reaction system. The amount of the chain transfer agent is usually from 5 to 20% by weight based on the total weight of the monomers.

In the step (1-b), the addition may be also carried out by a per se conventional procedure. For instance, the isocyanatocarbonyl group-containing polymer is reacted with the functional group-containing compound (II) in an inert solvent at a temperature of −20° to 100° C., preferably of 0° to 80° C., more preferably at room temperature or under cooling with ice.

According to the second process, the functional polymer of the invention can be produced by (2-a) addition of the functional group-containing compound (II) to the isocyanato group in the alkenoyl isocyanate (I) to give a functional group-introduced isocyanatocarbonyl group-containing compound and (2-b) polymerization of the functional group-introduced isocyanatocarbonyl group-containing compound optionally with one or more polymerizable monomers.

In the step (2-a), the addition may be carried out by a per se conventional procedure. For instance, the alkenoyl isocyanate (I) is reacted with the functional group-containing compound (II) in an inert solvent at a temperature of −20° to 100° C., preferably of 0° to 80° C., more preferably at room temperature or under cooling with ice.

In the step (2-b), the polymerization may be also carried out by a per se conventional procedure, particularly by solution polymerization. For instance, a monomeric mixture comprising the functional group-introduced isocyanatocarbonyl group-containing compound and optionally one or more polymerizable monomers in an inert solvent, preferably comprising a polymerization initiator is maintained at a temperature of 20° to 200° C., favorably of 60° to 150° C., more favorably of 80° to 120° C. for about 0.5 to 5 hours. The content of the functional group-introduced isocyanatocarbonyl group-containing compound in the total weight of the monomers is to be not less than 0.1% by weight. The amount of the polymerization initiator may be, when used, from 0.1 to 10% by weight, preferably from 0.5 to 5% by weight, based on the total weight of the monomers. When desired, a chain transfer agent may be also present in the reaction system. The amount of the chain transfer agent is usually from 5 to 20% by weight based on the total weight of the monomers.

The starting alkenoyl isocyanate (I) can be produced by reacting an alkenylamide of the formula:

$$CH_2=\underset{\underset{R}{|}}{C}-CONH_2 \quad (III)$$

wherein R is as defined above and an oxalyl halide of the formula:

$$(COX)_2 \quad (IV)$$

wherein X is as defined above, optionally followed by dehydrohalogenation of the by-produced haloalkanoyl isocyanate of the formula:

$$CH_2X-CH-\underset{\underset{O}{\|}}{C}-NCO \quad (V)$$
$$\phantom{CH_2X-C}\overset{\overset{R}{|}}{H}$$

wherein R and X are each as defined above. More advantageously, the alkenoyl isocyanate (I) can be produced by reacting the alkenylamide (III) with the oxalyl halide (IV) to produce an alkenyloxazolinedione hydrohalide of the formula:

$$\begin{array}{c}\overset{\oplus}{HN}\text{———}C=O\\ \| \quad\quad\quad | \\ CH_2=C-C \quad\quad C=O \\ | \quad\ \ \backslash\ /\\ R \quad\quad\ O\end{array} \cdot X^{\ominus} \quad (VI)$$

wherein X is a halogen atom (e.g. chlorine, bromine) and subjecting the latter to decomposition.

For production of the alkenyloxazolinedione hydrohalide (VI), it is preferred that the oxalyl halide (IV) is first charged into a reactor and then the alkenylamide (III) is portionwise added thereto, whereby the reaction proceeds. The molar ratio of the alkenylamide (III) and the oxalyl halide (IV) may be usually about 1:1-3, preferably about 1:1-1.5. The use of an inert solvent as the reaction medium is not essential but is usually preferred. Thus, either one or both of the alkenylamide (III) and the oxalyl halide (IV) may be previously dissolved or suspended therein. The reaction temperature is normally higher than −50° C. and lower than the decomposition temperature of the alkenyloxazolinedione hydrohalide (VI), preferably from about 0° to 40° C. From the industrial viewpoint, the temperature around room temperature or under ice cooling is favorable.

For separation of the alkenyloxazolinedione hydrohalide (VI) from the reaction mixture, there may be adopted any per se conventional separation procedure such as filtration or distillation under reduced pressure. Addition of seed crystals of the alkenyloxazolinedione hydrohalide (VI) to the reaction mixture may be sometimes favorable to accelerate the precipitation of the alkenyloxazolinedione hydrohalide (VI). However, separation of the alkenyloxazolinedione hydrohalide (VI) from the reaction mixture is not necessarily required.

The alkenyloxazolinedione hydrohalide (VI) is then subjected to decomposition under the condition affording the alkenoyl isocyanate (I) predominantly or suppressing by-production of the haloalkanoyl isocyanate (V). One typical example of such condition is to carry out the decomposition under an ordinary pressure (atmospheric or autogenic). Namely, the alkenyloxazolinedione hydrohalide (VI) as charged in a reactor is heated under an ordinary pressure until the decomposition proceeds sufficiently. When a reaction medium is used, the heat decomposition can take place at such a low temperature as about 40° C. In the absence of any reaction medium, heating up to the decomposition temperature of the 2-alkanoyloxazolinedione hydrohalide (e.g. about 102° to 103° C. in case of 2-isopropenyloxazoline-4,5-dione hydrochloride) is required. As the reaction medium, there may be used an inert solvent. Another example of the condition is to carry out the decomposition in the presence of a hydrogen halide-eliminating agent. Namely, decomposition of the alkenoyloxazoline hydrohalide (VI) in the presence of a hydrogen halide-eliminating agent at a temperature of −50° to 200° C., preferably from 0° to 150° C. under an ordinary or reduced pressure gives predominantly the alkenoyl isocyanate (I). As the hydrogen halide-eliminating agent such as not having an active hydrogen atom or as being reacted with a hydrogen halide not to produce an active hydrogen atom is favorably used. Amines which are the most popular hydrogen halide-eliminating agents are hardly usable in the process of this invention. Specific examples of the preferred hydrogen halide-eliminating agent are metal complex compounds (e.g. $(Ph_3P)_2Ru(CO)_3$, $(Ph_3P)_3Pt$, metal halides (e.g. lithium chloride, titanium tetrachloride, aluminum chloride, cuprous chloride), synthetic zeolite (e.g. molecular sieve, microporous glass), etc. The hydrogen halide-eliminating agent is used normally in an amount of about 0.1 to 100 mol, preferably of about 0.1 to 10 mol to 1 mol of the alkenyloxazolinedione hydrohalide (VI). Any reaction medium is not necessarily required to use. When used, an inert solvent may be employed. Another example of the condititition is to carry out the decomposition in the presence of a liquid medium having a dielectric constant of not more than 4. Such liquid medium may be constituted with one or more of inert solvents chosen from aliphatic or alicyclic hydrocarbons (e.g. pentane, hexane, heptane, octane, decalin, cyclohexane), aromatic hydrocarbons (e.g. benzene, toluene, xylene, naphthalene), ethers (e.g. propyl ether, butyl ether, dioxane, isopropyl ether), esters, halogenated hydrocarbons (e.g. carbon tetrachloride), etc. A dielectric constant of not more than 4 may be attained by the use of a single solvent or by the use of two or more solvents in combination. The decomposition may be carried out by keeping the alkenyloxazolinedione hydrohalide (VI) in a liquid medium of not more than 4 in dielectric constant at a temperature higher than the decomposition temperature of the alkenyloxazolinedione hydrohalide (VI), usually from about 40° to 150° C., preferably from about 60° to 120° C., whereby the alkenoyl isocyanate (I) is predominantly produced.

Recovery of the alkenoyl isocyanate (I) from the reaction mixture may be accomplished by a per se conventional separation procedure such as distillation under atmospheric or reduced pressure.

In any of the above reactions and the post-treatments, a small amount of a polymerization inhibitor may be incorporated into the reaction system or the reaction mixture for prevention of the unnecessary polymerization on the double bond. Examples of the polymerization inhibitor are hydroquinone, p-methoxyphenol, 2,6- di-t-butyl-4-methylphenol, 4-t-butylcatechol, bisdihydroxybenzylbenzene, 2,2'-methylene-bis(6-t-butyl-3-methylphenol), 4,4'-butylidene-bis(6-t-butyl-3-methylphenol), 4,4'-thiobis(6-t-butyl-3-methylphenol), p-nitrosophenol, diisopropylxanthogenesulfide, N-nitrosophenylhydroxylamine ammonium salt, 1,1-diphenyl-2-picrylhydrazil, 1,3,5-triphenylpheldazyl, 2,6-di-t-butyl-alpha-(3,5-di-t-butyl-4-oxo-2,5-cyclohexadien-1-ylidene)-p-trioxy, 2,2,6,6-tetramethyl-4-piperidone-1-oxil, dithiobenzoyl sulfide, p,p'-ditolyl trisulfide, p,p'-ditolyl tetrasulfide, dibenzyl tetrasulfide, tetraethylthiuram disulfide, etc.

The alkenoyl isocyanates (I) are, in general obtained in a liquid stable at room temperature and therefore can be handled with ease. They are soluble in various organic solvents and can be used in their solution form.

The other polymerizable monomers usable in the step (1-a) of the first process are those having no active hydrogen atom, while the ones usable in the step (2-b) of the second process may be chosen from polymeriable monomers having no active hydrogen atom and polymerizable monomers having an active hydrogen atom. Examples of the polymerizable monomers having no active hydrogen atom are monoolefinic or diolefinic hydrocarbons (e.g. styrene, alphamethylstyrene, alpha-ethylstyrene, 2-methylpropane-1, 2-methylbutene-1, 2-methylpentene-1, 2,3-dimethylbutene-1, 2,3-dimethylpentene-1, 2,4-dimethylpentene-1, 2,3,3-trimethylheptene-1, 2,3-dimethylhexene-1, 2,4-dimethylhexene-1, 2,5-dimethylhexene-1, 2-methyl-3-ethylpentene-1, 2,3,3-trimethylpentene-1, 2,3,4-trimethylpentene-1, 2-methyloctene-1, 2,6-dimethylheptene-1, 2,6-dimethyloctene-1, 2,3-dimethyldecene-1, 2-methylnonadecene-1, ethylene, propylene, butylene, amylene, hexylene, butadiene-1,3, isoprene), monoolefinic or diolefinic halogenated hydrocarbons (e.g. alpha-chlorostyrene, alpha-bromostyrene, 2,5-dichlorostyrene, 2,5-dibromostyrene, 2,6-dichlorostyrene, 3,4-dichlorostyrene, o-, m- or p-fluorostyrene, 2,6-difluorostyrene, 3-fluoro-4-chlorostyrene, 3-chloro-4-fluorostyrene, 2,4,5-trichlorostyrene, dichloromonofluorostyrene, 2-chloropropene, 2-chlorobutene, 2-chloropentene, 2-chlorohexane, 2-chloroheptene, 2-bromobutene, 2-bromoheptene, 2-fluorohexene, 2-fluorobutene, 2-iodopropene, 2-iodopentene, 4-bromoheptene, 4-chloroheptene, 4-fluoroheptene, cis- and trans-1,2-dichloroethylene, 1,2-dibromoethylene, 1,2-difluoroethylene, 1,2-diiodoethylene, vinyl chloride, vinylidene chloride, bromoethylene, fluoroethylene, iodoethylene, 1,1-dibromoethylene, 1,1-difluoroethylene, 1,1-diiodoethylene, 1,1,2-trifluoroethylene, chlorobutadiene), carboxylic alkenyl esters (e.g. vinyl acetates, vinyl propionate, vinyl butyrate, vinyl isobutyrate, vinyl valerate, vinyl caproate, vinyl enantate, vinyl benzoate, vinyl p-chlorobenzoate, vinyl o-chlorobenzoate, vinyl p-methoxybenzoate, vinyl p-ethoxybenzoate, isopropenyl acetate, isopropenyl propionate, isopropenyl butyrate, isopropenyl isobutyrate, isopropenyl valerate, isopropenyl caproate, isopropenyl enanteate, isopropenyl benzoate, isopropenyl p-chlorobenzoate, isopropenyl o-chlorobenzoate, isopropenyl o-bromobenzoate, isopropenyl m-chlorobenzoate, isopropenyl alpha-chloroacetate, isopropenyl alpha-bromopropionate, vinyl alpha-chloroacetate, vinyl alpha-bromoacetate, vinyl alpha-chloropropionate, vinyl alpha-bromopropionate, vinyl alpha-iodopropionate, vinyl alpha-chlorobutyrate, vinyl alpha-chlorovalerate, vinyl alpha-bromovalerate), alkyl alkenoates (e.g. methyl acrylate, ethyl acrylate, n-propyl acrylate, isopropyl acrylate, n-butyl acrylate, sec-butyl acrylate, t-butyl acrylate, isobutyl acrylate, n-hexyl acrylate, 2-ethylhexyl acrylate, 3,5,5-trimethylhexyl acrylate, n-octyl acrylate, lauryl acrylate, tridecyl acrylate, stearyl acrylate, methyl methacrylate, ethyl methacrylate, n-propyl methacrylate, isopropyl methacrylate, n-butyl methacrylate, sec-butyl methacrylate, t-butyl methacrylate, isobutyl methacrylate, amyl methacrylate, n-hexyl methacrylate, 2-ethylhexyl methacrylate, n-octyl methacrylate, lauryl methacrylate, tridecyl methacrylate, stearyl methacrylate, methyl crotonate), alkyl substituted alkenoates (e.g. methyl alpha-chloroacrylate, methyl alpha-bromoacrylate, methyl alpha-fluoroacrylate, methyl alpha-iodoacrylate, ethyl alpha-chloroacrylate, propyl alpha-chloroacrylate, isopropyl alpha-bromoacrylate, amyl alpha-chloroacrylate, decyl alpha-chloroacrylate, methyl alpha-cyanoacrylate, ethyl alpha-cyanoacrylate, amyl alpha-cyanoacrylate, decyl alpha-cyanoacrylate), allyl or methallyl compounds (e.g. allyl chloride, allyl cyanide, allyl bromide, allyl fluoride, allyl iodide, allyl chloride carbonate, allyl nitrate, allyl thiocyanate, allyl formate, allyl acetate, allyl propionate, allyl valerate, allyl caproate, allyl 3,5,5-trimethylhexoate, allyl benzoate, allyl acrylate, allyl crotonate, allyl oleate, allyl chloroacetate, allyl trichloroacetate, allyl chloropropionate, allyl chlorovalerate, allyl lactate, allyl pyruvate, allyl aminoacetate, allyl acetoacetate, allyl thioacetate, methallyl chloride, methallyl cyanide, methallyl chloride carbonate, methallyl nitrate, methallyl thiocyanate, methallyl formate, methallyl acetate, methallyl propionate, methallyl valerate, methallyl caproate, methallyl benzoate, allyl acrylate, allyl crotonate, allyl oleate, methallyl chloroacetate, methallyl trichloroacetate, methallyl chloropropionate, methallyl chlorovalerate, methallyl pyruvate, methallyl acetoacetate, methallyl thioacetate), dialkylaminoalkyl alkanoates (e.g. N,N'-dimethylaminoethyl acrylate, N,N'-dimethylaminoethyl methacrylate), isocyanatoalkyl alkanoates (e.g. isocyanatomethyl acrylate, isocyanatoethyl acrylate, isocyanatomethyl methacrylate, isocyanatoethyl methacrylate), glycidyl acrylate, glycidyl methacrylate, cyclohexyl acrylate, cyclohexyl methacrylate, phenyl acrylate, phenyl methacrylate, benzyl acrylate, benzyl methacrylate, dialkyl unsaturated carboxylates (e.g. dimethyl maleate, diethyl maleate, dimethyl fumarate, diethyl fumarate, dibutyl fumarate), unsaturated nitriles (e.g. acrylonitrile, methacrylonitrile, ethacrylonitrile, 3-octenenitrile, crotonitrile, oleonitrile), etc. Examples of the polymerizable monomer having an active hydrogen atom are unsaturated carboxylic acids (e.g. acrylic acid, methacrylic acid, crotonic acid, cinnamic acid, 2-isopropylacrylic acid, alpha-chloroacrylic acid), monoesters of alkyleneglycols with unsaturated carboxylic acids (e.g. ethylene glycol monoacrylate, propylene glycol monoacrylate, ethylene glycol monomethacrylate, ethylene glycol monocrotonate), unsaturated alcohols (e.g. crotyl alcohol, cinnamyl alcohol), unsaturated amides (e.g. acrylamide, methacrylamide, crotonamide, cinnamamide, p-benzamidostyrene), acrylic acid 2-sulfoethyl, methacrylic acid 2-sulfoethyl, t-butylacrylamidosulfonic acid, acrylic acid 4-sulfophenyl, p-vinylbenzenesulfonic acid, 2-methacryloxyethyl acid phosphate, 3-chloro-2-acid phosphoxypropyl methacrylate, vinyl phosphate, isopropenyl phosphate, unsaturated amines (e.g. allylamine, o-aminostyrene, methacrylic acid t-butylaminoethyl, 7-amino-3,7-dimethyloctyl acrylate), etc.

Likewise, the inert solvent usable in the steps (1-a) and (1-b) of the first process and in the step (2-a) of the second process is to be chosen from the ones having no active hydrogen atom, while the inert solvent usable in the step (2-b) of the second process may be chosen from the ones having no active hydrogen atom and the ones having an active hydrogen atom. Examples of the inert solvent having no active hydrogen atom are aliphatic hydrocarbons (e.g. pentane, hexane, heptane), aromatic hydrocarbons (e.g. benzene, toluene, xylene), alicyclic hydrocarbons (e.g. cyclohexane, methylcyclohexane, decalin), petrolic hydrocarbons (e.g. petroleum ether, petroleum benzin), halogenated hydrocarbons (e.g. carbon tetrachloride, chloroform, 1,2-dichloroethane), ethers (e.g. diethyl ether, diisopropyl ether, anisole, dioxane, tetrahydrofuran), esters (e.g. methyl acetate, ethyl acetate, butyl acetate), ketones (e.g. acetone, methylethylketone, methylisobutylketone, cyclohexanone, acetophenone, isophorone), acetonitrile, dimethylformamide, dimethylsulfoxide, etc.

As the polymerization initiator usable in the step (1-a) of the first process and in the step (2-b) of the second process, there are exemplified organic peroxides (e.g. benzoyl peroxide, t-butyl perbenzoate, t-butyl peroxide, cumene hydroperoxide, di-t-butyl peroxide, t-butyl peroctoate), azo compounds (e.g. 2,2'-azobisisobutyronitrile, dimethyl azodiisobutyrate, 2,2'-azobis(2,4-dimethylvaleronitrile), 2,2'-azobis(4-methoxy-2,4-dimethylvaleronitrile), etc. As the chain transfer agent, there may be used any conventional one having no active hydrogen atom. Specific examples include alpha-methylstyrene dimer.

The isocyanatocarbonyl group-containing polymer as obtained in the step (1-a) of the first process has usually an isocyanatocarbonyl group content of 0.1 to 72.2% by weight and a molecular weight of about 1,000 to 100,000.

Depending upon the kind of the functional group-containing compound (II) as used in the step (1-b) of the first process or in the step (2-a) of the second process, there is obtainable the functional polymer having characteristic physical properties.

When, for instance, the functional group-containing compound (II) is a fluorinated compound containing an active hydrogen atom of the formula:

Rf—H  (II-a)

wherein Rf is the residue of the fluorinated compound excluding the active hydrogen atom therefrom, there is obtained a functional polymer comprising a main chain of carbon-carbon bonds and a pendant group of the formula:

—CO—NH—CO—Rf wherein Rf is as defined above appended to the main chain. Such functional polymer has usually a molecular weight of 1,000 to 100,000 and a content of said pendant group of 0.1 to 99.9% by weight.

Examples of the fluorinated compound (II-a) are o-, m-, p-aminobenzotrifluoride, 2-amino-5-bromobenzotrifluoride, 3-amino-4-bromobenzotrifluoride, 5-amino-2-bromobenzotrifluoride, 2-amino-5-chlorobenzotrifluoride, 3-amino-4-chlorobenzotrifluoride, 5-amino-2-chlorobenzotrifluoride, 2-amino-5-fluorobenzotrifluoride, 3-amino-4-fluorobenzotrifluoride, 5-amino-2-fluorobenzotrifluoride, 3-amino-5-methoxybenzotrifluoride, 2-amino-5nitrobenzotrifluoride, 4-amino-3-nitrobenzotrifluoride, 5-amino-2-nitrobenzotrifluoride, 4-amino-2,3,5,6-tetrafluorobenzamide, 4-amino-2,3,5,6-tetrafluorobenzoic acid, 4-amino-2,3,5,6-tetrafluorobenzonitrile, bis(trifluoromethylacetamide), chlorodifluoroacetamide, chlorodifluoroacetic acid, 3-chloro-4-fluoroaniline, 2-chloro-6-fluorobenzoic acid, 3-chloro-4-fluorobenzoic acid, 2-chloro-6-fluorobenzyl alcohol, 2-chloro-4-fluorophenol, 2-chloro-6-fluorophenyl acetic acid, 1-chloro-3-fluoro-2-propanol, 4-chloro-3-hydroxybenzotrifluoride, decafluorobenzohydrol, 3,4-diaminobenzotrifluoride, 3,5-diaminobenzotrifluoride, 4,4'-diaminooctafluorobiphenyl, 1,3-dichlorotetrafluoroisopropanol, difluoroacetic acid, 2,4-difluoroaniline, 2,5-difluoroaniline, 2,6-difluoroaniline, 2,4-difluorobenzamide, 2,5-difluorobenzamide, 2,6-difluorobenzamide, 3,4-difluorobenzamide, 2,4-difluorobenzoic acid, 2,5-difluorobenzoic acid, 2,6-difluorobenzoic acid, 3,4-difluorobenzoic acid, 1H,1H-heptadecafluoroctanol, etc.

The thus obtained functional polymer wherein the functional group is a fluorinated group has physical characteristics attributed to the fluorinated group and to the carbonyliminocarbonyl linkage. Namely, the functional polymer has good water- and oil-repellency, low stickiness and small surface friction coefficient due to the fluorinated group and good toughness and high adhesion due to the carbonyliminocarbonyl linkage. Thus, the surface characteristics can be appropriately controlled. Besides, their carbon-fluorine bonds and mimic effects may contribute in exertion of agro-chemical effect. Accordingly, the functional polymer is useful as a resinous material for coating compoitions, engineering plastics, elastomers and agrochemicals.

When the functional group-containing compound (II) is an aminotriazine compound containing an active hydrogen atom of the formula:

Rm—H  (II-b)

wherein Rm is the residue of the aminotriazine compound excluding the active hydrogen atom therefrom, there is obtained a functional polymer comprising a main chain of carbon-carbon bonds and a pendant group of the formula:

—CO—NH—CO—Rm wherein Rm is as defined above appended to the main chain. Such functional polymer has usually a molecular weight of 1,000 to 100,000 and a content of said pendant group of 0.1 to 99.9 % by weight.

Examples of the aminotriazine compound (II-b) are melamine and its modified or related derivatives such as melamine, methylolated melamines (e.g. monomethylolmelamine, dimethylolmelamine, trimethylolmelamine, tetramethylolmelamine, pentamethylolmelamine, hexamethylolmelamine) and alkanol-modified methylolated melamines (e.g. methoxymethylolmelamine, ethoxymethylolmelamine, propoxymethylolmelamine), guanamine and its modified or related derivatives (e.g. homoguanamine, acetoguanamine, benzoguanamine, phenylacetoguanamine, methoxyguanamine), etc.

The thus obtained functional polymer wherein the functional group is an aminotriazine group has physical characteristics attributed to the aminotriazine group and to the carbonyliminocarbonyl linkage. Namely, the functional polymer has good crosslinkability and high rigidity due to the aminotriazine group and good toughness and high adhesion due to the carbonyliminocarbonyl linkage. Besides, it will serve to improve the storage stability and suppress the self-condensation. Accordingly, the functional polymer is useful as a resinous material for coating compoitions, engineering plastics and elastomers.

When the functional group-containing compound (II) is a photosensitive compound containing an active hydrogen atom of the formula:

$$Rp\text{—}H \qquad (\text{II-c})$$

wherein Rp is the residue of the photosensitive compound excluding the active hydrogen atom therefrom, there is obtained a functional polymer comprising a main chain of carbon-carbon bonds and a pendant group of the formula:

$$-\text{CO}-\text{NH}-\text{CO}-Rp$$

wherein Rp is as defined above appended to the main chain. Such functional polymer has usually a molecular weight of 1,000 to 100,000 and a content of said pendant group of 0.1 to 99.9% by weight.

Examples of the photosensitive compound (II-c) are photosensitive group-bearing alcohols, thiols, carboxylic acids, thiocarboxylic acids, amines, etc. As the photosensitive group, there may be exemplified olefin, cinnamoyl, cinnamylidene, cinnamylideneacetyl, furylacryloyl, coumarin, pyrone, benzalacetophenone, styrylpyridine, anthracene, stilbene, alpha-phenylmaleimide, azido, phenylazido, sulfonylazido, carbonylazido, diazo, alpha-quinonediazido, benzophenone, benzoin, 1,3-dioxane, dithiocarbamate, xanthete, 1,2,3-thiadiazole, cyclopropene, azadioxabicyclo, spiropyrane, etc. Thus, specific examples of the photosensitive compound (II-c) are benzoin, acetoin, p-hydroxybenzaldehyde, 1,4,9,10-tetrahydroxyanthracene, benzhydrol, ascorbic acid, benzylic acid, 4-methoxyphenol, p-nitrophenol, 2-mercaptobenzothiazole, p-aminoacetophenone, thiocynamine, etc. Alcoholic, thiolic, carboxylic, thiocarboxylic and amino derivatives of benzophenone, acetophenone, 9-fluorosoneacetophenone, alpha-benzoylbenzoic acid, benzylphenylketone, propiophenone, benzalacetophenone, benzoylacetone, benzaldehyde, etc. are also usable.

The thus obtained functional polymer wherein the functional group is an photosensitive group has physical characteristics attributed to the photosensitive group and to the carbonyliminocarbonyl linkage. Namely, the functional polymer has high curability with irradiation of ultraviolet rays due to the photosensitive group and good toughness and high adhesion due to the carbonyliminocarbonyl linkage. Accordingly, the functional polymer is useful as a photo-curable resinous material for coating compoitions, engineering plastics and elastomers.

When the functional group-containing compound (II) is a bicyclo or spiro structure compound containing an active hydrogen atom of the formula:

$$Rb\text{—}H \qquad (\text{II-d})$$

wherein Rb is the residue of the bicyclo or spiro structure compound excluding the active hydrogen atom therefrom, there is obtained a functional polymer comprising a main chain of carbon-carbon bonds and a pendant group of the formula:

$$-\text{CO}-\text{NH}-\text{CO}-Rb$$

wherein Rb is as defined above appended to the main chain. Such functional polymer has usually a molecular weight of 1,000 to 100,000 and a content of said pendant group of 1.0 to 92% by weight.

As the bicyclo or spiro structure compound (II-d), there may be used any one representable by either one of the following formulas:

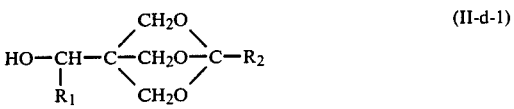  (II-d-1)

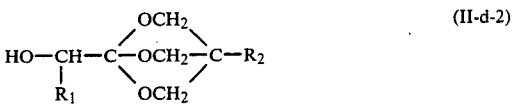  (II-d-2)

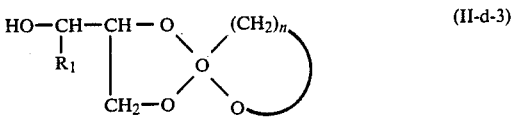  (II-d-3)

wherein $R_1$ and $R_2$ are each a hydrogen atom or a lower alkyl group (e.g. methyl, ethyl, propyl) and n is an integer of 3 to 5. Specific examples are 1-methyl-4-hydroxymethyl-2,6,7-trioxabicyclo[2.2.2]octane, 1-ethyl-4-hydroxymethyl-2,6,7-trioxabicyclo[2.2.2]octane, 4-ethyl-1-hydroxymethyl-2,6,7-trioxabicyclo[2.2.2]octane, 2-hydroxymethyl-1,4,6-trioxaspiro[4.4]nonane, 2-hydroxymethyl-1,4,6-trioxaspiro[4.5]decane, 2-hydroxymethyl-1,4,6-trioxaspiro[4.6]undecane, etc.

The thus obtained functional polymer wherein the functional group is a bicyclo or spiro structure group has physical characteristics attributed to the bicyclo or spiro structure group and to the carbonyliminocarbonyl linkage. Namely, the functional polymer shows good crosslinkability in the presence or absence of a catalyst due to the bicyclo or spiro structure group and good toughness and high adhesion due to the carbonyliminocarbonyl linkage. As the catalyst, there may be used a Lewis acid, and specific examples of the catalyst are boron trifluoride, silicotungstic acid, phosphomolybdic acid, zinc chloride, trimellitic acid, diphenyliodonium hexafluorophosphate, tin tetrachloride, ferric chloride, heteropolyacids, organic acids, etc. For formation of a cured coating film, the functional polymer admixed with a catalyst may be allowed to stand at room temperature for 1 to 2 days after the application onto a substrate. Alternatively, the functional polymer admixed or not with a catalyst may be subjected to baking after the application. The amount of the catalyst to be admixed may be from 0.1 to 10% by weight, preferably from 1 to 5% by weight of the functional polymer. The heating temperature for baking may be usually from 120° to 180° C., although this is not limitative.

Accordingly, the functional polymer is useful as a curable resinous material for coating compoitions, sealers, adhesive agents, engineering plastics and elastomers. It is particularly notable that the use of the functional polymer can afford a coating film which is highly water-resistant.

Practical and presently preferred embodiments of the invention are illustratively shown in the following examples wherein part(s) and % are by weight, unless otherwise indicated.

REFERENCE EXAMPLE 1

Preparation of 2-vinyloxazoline-4,5-dione hydrochloride:

Oxalyl chloride (130 g; 1.02 mol) was charged in a reactor, and a warm solution of acrylamide (71 g; 1.0 mol) in dichloroethane (250 ml) was dropwise added thereto (reaction temperature, 10° to 30° C.). After completion of the dropwise addition, the solvent and excess of the oxalyl chloride were removed by distillation under reduced pressure to obtain 2-vinyloxazoline-4,5-dione hydrochloride (161 g) as a yellow oil. Viscosity, 100,000 cp.

REFERENCE EXAMPLE 2

Preparation of 2-isopropenyloxazoline-4,5-dione hydrochloride:

A warm solution of methacrylamide (21.25 g) in dichloroethane (90 ml) was dropwise added in 1 hour to oxalyl chloride (34.5 g) kept at room temperature (20° C.) while stirring. The resultant mixture was cooled with water to room temperature. The produced 2-isopropenyloxazoline-4,5-dione hydrochloride (37 g) was collected by filtration under suction, washed with hexane and dried under reduced pressure. Decomposition temperature, 102° to 103° C.

REFERENCE EXAMPLE 3

Preparation of methacryloyl isocyanate:

To 2-isopropenyloxazoline-4,5-dione hydrochloride (200 g), o-dichlorobenzene (800 g) was added, and the resultant mixture was heated to 140° C. while stirring for about 40 minutes. After cooling with water, the reaction mixture was distilled under reduced pressure to give methacryloyl isocyanate (70.9 g; b.p., 52° to 53° C./39 mmHg) as a colorless liquid and alpha-methyl-beta-chloropropionyl isocyanate (48.7 g).

REFERENCE EXAMPLE 4

Preparation of acryloyl isocyanate:

To 2-vinyloxazoline-4,5-dione hydrochloride (100 g), o-dichlorobenzene (400 g) was added, and the resultant mixture was heated at 110° to 120° C. while stirring for about 30 minutes. After cooling with ice, the reaction mixture was distilled under reduced pressure to give acryloyl isocyanate (8.9 g; b.p., 82° to 83° C./760 mmHg) and betachloropropionyl isocyanate (56.4 g).

REFERENCE EXAMPLE 5

(1) Preparation of 2-isopropenyloxazoline-4,5-dione hydrochloride:

Oxalyl chloride (139.6 g) and o-dichlorobenzene (400 g; dielectric constant, 9.88) were mixed together and cooled to a temperature of 0° to 10° C. Methacrylamide (85.1 g) was portionwise added thereto in 40 minutes, followed by stirring at 35° to 40° C. for 2 hours. A small amount of seed crystals of 2-isopropenyloxazoline-4,5-dione hydrochloride was added thereto, and the resultant mixture was allowed to stand whereby 2-isopropenyloxazoline-4,5-dione hydrochloride was crystallized out.

(2) Preparation of methacryloyl isocyanate:

To the above mixture comprising crystals of 2-isopropenyloxazoline-4,5-dione hydrochloride, hexane (600 g; dielectric constant, 1.88) was added so that dielectric constant of the solvent mixture was made to 3.45. Stirring was continued at a temperature of 70° to 75° C. for 1.5 hours. Distillation of the reaction mixture gave methacryloyl isocyanate (55.9 g).

REFERENCE EXAMPLE 6

(1) Preparation of 2-isopropenyloxazoline-4,5-dione hydrochloride:

Oxalyl chloride (139.6 g; 1.1 mol) and o-dichlorobenzene (400 g; dielectric constant, 9.88) were mixed together and cooled to a temperature of 0° to 10° C. Methacrylamide (85.1 g; 1.0 mol) was portionwise added thereto in 40 minutes. A small amount of seed crystals of 2-isopropenyloxazoline-4,5-dione hydrochloride was added thereto, and the resultant mixture was allowed to stand whereby 2-isopropenyloxazoline-4,5-dione hydrochloride was crystallized out. Hexane (600 g; dielectric constant, 1.88) was added thereto. Precipitated crystals were collected by filtration to obtain 2-isopropenyloxazoline-4,5-dione hydrochloride in a yield of 98.6%.

(2) Preparation of methacryloyl isocyanate:

2-Isopropenyloxazoline-4,5-dione hydrochloride as obtained above (100 g) was suspended in a mixture of hexane (240 g) and o-dichlorobenzene (160 g), the dielectric constant of the solvent mixture being 3.45. The suspension was heated at a temperature of 70° to 75° C. under reflux for 1.5 hours. Distillation of the reaction mixture gave methacryloyl isocyanate (49 g; yield, 89.9%) and alpha-methyl-beta-chloropropionyl isocyanate (1.4 g; yield, 1.7%).

EXAMPLE 1

(1) Preparation of di(trifluoromethyl)methanol/methacryloyl isocyanate adduct:

Into a reaction vessel purged with nitrogen gas, di(trifluoromethyl)methanol was dissolved in chloroform, and a solution of methacryloyl isocyanate in 1,2-dichloroethane was dropwise added thereto while stirring in nitrogen stream. After completion of the dropwise addition, chloroform and 1,2-dichloroethane were removed by distillation under reduced pressure to give di(trifluromethyl)methanol/methacryloyl isocyanate adduct. M.P., 112.5°–113° C.

(2) Preparation of a fluorinated group-containing polymer:

A mixture of methyl methacrylate (8.0 parts), n-butyl acrylate (8.0 parts), styrene (4.0 parts), di(trifluoromethyl)methanol/methacryloyl isocyanate adduct (2.0 parts) and 2,2'-azobis(2,4-dimethylvaleronitrile) (0.5 part) was dropwise added to toluene (33.0 parts) heated at 150° to 110° C. in 1.5 hours. After the dropwise addition was completed, stirring was continued at the same temperature for 3 hours to produce a fluorinated group-containing polymer. Molecular weight (determined by gel permeation chromatography), 14,900. Non-volatile content, 33.8%.

EXAMPLE 2

(1) Preparation of an isocyanatocarbonyl group-containing polymer:

A mixture of methacryloyl isocyanate (1.11 parts), methyl methacrylate (8.0 parts), n-butyl acrylate (8.0 parts), styrene (4.0 parts) and 2,2'-azobis(2,4-dimethylvaleronitrile) (0.53 part) was dropwise added to xylene (50.0 parts) heated at 113° C. in 1.5 hours. After the dropwise addition was completed, stirring was continued at the same temperature for 3 hours to produce an isocyanatocarbonyl group-containing polymer.

(2) Preparation of a fluorinated group-containing polymer:

To the reaction mixture comprising the isocyanatocarbonyl group-containing polymer as above obtained, a solution of 1H,1H-pentadecafluorooctanol (4.0 g) in a mixture of xylene/chloroform/ethyl acetate was dropwise added thereto at about 110° C. After completion of the dropwise addition, the reaction mixture was cooled with water to give a fluorinated group-containing polymer. Molecular weight, 7,400. Non-volatile content, 18%.

EXAMPLE 3

(1) Preparation of butylated melamine/methacryloyl isocyanate adduct:

Into a reaction vessel purged with nitrogen gas, butylated melamine was dissolved in chloroform, and a solution of methacryloyl isocyanate in 1,2-dichloroethane was dropwise added thereto while stirring in nitrogen stream. After completion of the dropwise addition, chloroform and 1,2-dichloroethane were removed by distillation under reduced pressure to give butylated melamine/methacryloyl isocyanate adduct as a colorless oil; molecular weight 1,160 (determined by GPC); viscosity, 23,000 cp.

(2) Preparation of an aminotriazine group-containing polymer:

A mixture of methyl methacrylate (20 parts), n-butyl acrylate (15 parts), butylated melamine/methacryloyl isocyanate adduct (15 parts) and 2,2'-azobis(2,4-dimethylvaleronitrile) (1.25 parts) was dropwise added to xylene (125 parts) heated at 100° to 105° C. in 2.0 hours. After the dropwise addition was completed, stirring was continued at the same temperature for 4 hours, followed by cooling with water to produce an aminotraizine group-containing polymer. Molecular weight (determined by gel permeation chromatography), 3,470. Non-volatile content, 24.1%.

EXAMPLE 4

Preparation of benzoin/methacryloyl isocyanate adduct:

In a reaction vessel purged with nitrogen gas, benzoin (2.12 g) was dissolved in chloroform (30 ml), and a solution of methacryloyl isocyanate (1.11 g) in 1,2-dichloroethane (7 g) was dropwise added thereto in 5 minutes while stirring in nitrogen stream, during which the inner temperature was elevated from 25° C. to 34° C. and then lowered. After completetion of the dropwise addition, chloroform and 1,2-dichloroethane were removed by distillation under reduced pressure to give benzoin/N-methacryloyl isocyanate adduct (i.e. N-methacryloylcarbamic acid benzoylbenzyl ester) (3.3 g). Recrystalization from a mixture of benzene and chloroform gave a colorless, transparent plates. M.P., 161°-163° C.

EXAMPLE 5

Preparation of p-hydroxybenzophenone/methacryloyl isocyanate adduct:

In a reaction vessel purged with nitrogen gas, p-hydroxybenzophenone (1.98 g) was dissolved in chloroform (10 ml), and a solution of methacryloyl isocyanate (1.11 g) in 1,2-dichloroethane (5 ml) was dropwise added thereto in 5 minutes while stirring in nitrogen stream. After completion of the dropwise addition, chloroform and 1,2-dichloroethane were removed by distillation under reduced pressure to give p-hydroxybenzophenone/methacryloyl isocyanate adduct (i.e. N-methacryloylcarbamic acid p-benzoylphenyl ester) (3.1 g). Recrystallization from a mixture of benzene and chloroform gave white granules. M.P., 96°-97° C.

EXAMPLE 6

Preparation of cinnamyl alcohol/methacryloyl isocyanate adduct:

In a reaction vessel purged with nitrogen gas, methacryloyl isocyanate (1.11 g) was dissolved in 1,2-dichloroethane (20 ml), and a solution of cinnamyl alcohol (1.34 g; 10 mmol) in 2-dichloroethane (20 ml) was dropwise added thereto in 10 minutes while stirring in nitrogen stream. After completion of the dropwise addition, 1,2-dichloroethane was removed by distillation under reduced pressure to give cinnamyl alcohol/methacryloyl isocyanate adduct (i.e. N-methacryloylcarbamic acid cinnamyl ester) (2.4 g) as a brown viscous liquid, which was washed with hexane and purified by silica gel column chromatography to give transparent needles. M.P., 66°-67° C.

EXAMPLE 7

(1) Preparation of an isocyanatocarbonyl group-containing polymer:

To a mixture of butyl acetate (8.0 g) and toluene (4.0 g) kept at 100° C., a mixture of methacryloyl isocyanate (4.0 g), 2-ethylhexyl acrylate (4.0 g), styrene (4.0 g) and 2,2'-azobis(2,4-dimethylvaleronitrile) (0.36 g) was dropwise added in two hours. A solution of 2,2'-azobis(2,4-dimethylvaleronitrile) (0.06 g) in toluene (3.0 g) was added thereto in 20 minutes, followed by aging for 50 minutes to give a copolymer of methacryloyl isocyanate, 2-ethylhexyl acrylate and styrene.

(2) Preparation of a photosensitive group-containing polymer:

The reaction mixture comprising the isocyanatocarbonyl group-containing polymer as obtained above was cooled to 35° C., and a solution of cinnamyl alcohol (4.9 g) in butyl acetate (5.0 g) was dropwise added thereto in 20 minutes. Addition of acetone (40.0 g) gave a yellowish milky solution comprising a photosensitive group-containing copolymer. Non-volatile content, 20.3%. Number average molecular weight, 4,591.

The above obtained copolymer solution was applied onto the surface of a glass plate by the aid of a doctor blade and allowed to stand at room temperature for 12 hours to give a coating film of 10$\mu$ in thickness. The glass plate having the coating film was passed through a ultraviolet ray irradiation apparatus (manufactured by Japan Storage Battery; output, 80 W/cm; light collector type; ozone generation type; line speed, 1 m/min, 1 pass) for curing. Evaluation of the cured coating film by acetone rubbing test gave the following results:

|  | Peeling off |
|---|---|
| Before irradiation | 6 times |
| After irradiation | 28 times |

EXAMPLE 8

(1) Preparation of an isocyanatocarbonyl group-containing polymer:

To butyl acetate (8.0 g) kept at 100° C., a mixture of methacryloyl isocyanate (2.0 g), 2-ethylhexyl acrylate (4.0 g), styrene (8.0 g) and 2,2'-azobis(2,4-dimethylvaleronitrile) (0.36 g) was dropwise added in 2 hours. A solution of 2,2'-azobis(2,4-dimethylvaleronitrile) (0.06 g) in toluene (3.0 g) was added thereto in 20 minutes, followed by aging for 30 minutes to give a copolymer of methacryloyl isocyanate, 2-ethylhexyl acrylate and styrene.

(2) Preparation of a photosensitive group-containing polymer:

The reaction mixture comprising the isocyanatocarbonyl group-containing polymer as obtained above was cooled to 35° C., and a solution of benzoin (3.8 g) in dioxane (40.0 g) was dropwise added thereto in 20 minutes, followed by aging for 30 minutes to give a solution comprising a photosensitive group-containing polymer (non-volatile content, 22.6%), which was then treated with hexane to give a copolymer having the molecule of benzoin added to obtain the photosensitive group containing polymer as prisms. Number average molecular weight, 7,884.

The above obtained copolymer solution was applied onto the surface of a glass plate by the aid of a doctor blade and allowed to stand at room temperature for 12 hours to give a coating film of 10μ in thickness. The glass plate having the coating film was passed through a ultraviolet ray irradiation apparatus (manufactured by Japan Storage Battery; output, 80 W/cm; light collector type; ozone generation type; line speed, 1 m/min, 2 pass) for curing. Evaluation of the cured coating film by acetone rubbing test gave the following results:

|  | Peeling off |
|---|---|
| Before irradiation | 6 times |
| After irradiation | 22 times |

EXAMPLE 9

(1) Preparation of 1-ethyl-4-hydroxymethyl-2,6,7-trioxabicyclo[2.2.2]octane/methacryloyl isocyanate adduct:

Into a reaction vessel, there were charged 1-ethyl-4-hydroxymethyl-2,6,7-trioxabicyclo[2.2.2]octane (5.28 g) and 1,2-dichloroethane (60 ml), and the resultant mixture was stirred at room temperature. Methacryloyl isocyanate (3.33 g) was dropwise added thereto in 5 minutes, and the resulting mixture was stirred at room temperature for 2 hours. The solvent was evaporated, and the residue was purified by silica gel column chromatography using a mixture of tetrahydrofuran and hexane as an eluent to obtain a compound of the formula:

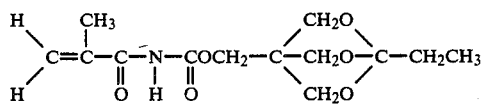

as crystals (5.6 g). M.P., 106°–109° C.

(2) Preparation of a bicyclo structure group-containing polymer:

To a reaction vessel, the above obtained adduct (25 g), methyl methacrylate (25 g) and dioxane (137 g) were charged, and a solution of azobisiobutyronitrile (0.5 g) in dioxane (20 g) was dropwise added thereto at 100° C. in 2 hours. After stirring at 100° C. for 30 minutes, a solution of azobisiobutyronitrile (0.25 g) in dioxane (10 g) was dropwise added thereto in 30 minutes. The resulting mixture was stirred at 100° C. for 1.5 hours to give a bicyclo structure group-containing polymer. Number average molecular weight 14,000.

EXAMPLE 10

The functional polymer obtained in Example 9 (10 g) was admixed with a solution of silicotungstic acid (hydrate) (0.06 g) in methylethylketone (2 g) to make a coating composition. The composition was applied onto the surface of a polished steel plate by the aid of a bar coater to make a coating film of 20 microns in thickness (after drying). The plate was subjected to baking at 120° C. for 30 minutes for curing. Evaluation of the pencil hardness and the solvent resistance of the cured coating film gave the following results: pencil hardness, 5H; resistant to rubbing of 50 times with acetone-immersed cloth.

EXAMPLE 11

(1) Preparation of methacryloyl isocyanate/methyl methacrylate/styrene/n-butyl acrylate copolymer:

Into a reaction vessel, butyl acetate (40 g) was charged, and heating was made to 100° C. A mixture of methacryloyl isocyanate (7.5 g), methyl methacrylate (17.5 g), styrene (15.0 g), n-butyl acrylate (10.0 g) and 2,2'-azobis(2,4-dimethylvaleronitrile) (0.5 g) was dropwise added thereto in 2 hours. After stirring at 100° C. for 30 minutes, a solution of 2,2'-azobis(2,4-dimethylvalernoitrile) (0.25 g) in butyl acetate (10 g) was dropwise added thereto at 100° C. in 30 minutes, followed by stirring at 100° C. in 1.5 hours to give a copolymer of methcaryloyl isocyanate with methyl methacrylate, styrene and n-butyl acrylate. Number average molecular weight, 10,500. Non-volatile content, 42.3%. Viscosity (determined by Gardner bubble viscometer), K<<L.

(2) Preparation of a bicyclo structure group-containing polymer:

To the copolymer as above obtained (20 g), a solution of 1-ethyl-4-hydroxymethyl-2,6,7-trioxabicyclo[2.2.2]octane (1.97 g) in dioxane (12.6 g) was dropwise added at room temperature, followed by stirring for 30 minutes to give a bicyclo structure group-containing polymer. Numver average molecular weight, 13,000.

What is claimed is:

1. A functional polymer having a main chain of carbon-carbon bonds and at least one functional group appended to the main chain with intervention of a carbonyliminocarbonyl linkage, the functional group being any one chosen from the group consisting of a fluorinated group, an aminotriazine group, a photosensitive group and a bicyclo or spiro struccture group and the content of the functional groups including the carbonyliminocarbonyl linkage in the molecule of the functional polymer being from 0.1 to 99.9% by weight.

2. The functional polymer according to claim 1, wherein the isocyanatocarbonyl group-containing polymer has a molecular weight of 1,000 to 100,000.

3. The functional polymer according to claim 1, wherein the functional group is a fluorinated group.

4. The functional polymer according to claim 1, wherein the functional group is an aminotriazine group.

5. The functional polymer according to claim 1, wherein the functional group is a photosensitive group.

6. The functional polymer according to claim 1, wherein the functional group is a bicyclo or spiro structure group.

7. The functional polymer which comprises units of an alkenoyl isocyanate of the formula:

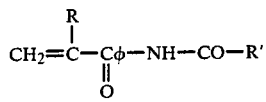

wherein R is a hydrogen atom or a lower alkyl group and R' is the residue of a functional group-containing compound excluding the active hydrogen atom therefrom, optionally with units of one or more of other polymerizable monomers having no active hydrogen atom.

8. A process for preparing the functional polymer according to claim 1, which comprises (1) polymerization of an alkenoyl isocyanate of the formula:

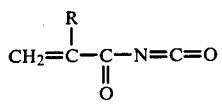

wherein R is a hydrogen atom or a lower alkyl group, optionally with one or more of other polymerizable monomers having no active hydrogen atom and addition of a functional group-containing compound having an active hydrogen atom of the formula:

R'—H wherein R' is the residue of a functional group-containing compound excluding the active hydrogen atom therefrom to the isocyanatocarbonyl group in the resultant isocyanatocarbonyl group-containing polymer, or (2) addition of the functional group-containing compound to the isocyanato group of the alkenoyl isocyanate and polymerization of the resulting functional group-introduced isocyanatocarbonyl group-containing compound optionally with one or more polymerizable monomers.

* * * * *